United States Patent
Karjalainen et al.

(10) Patent No.: US 6,714,812 B1
(45) Date of Patent: Mar. 30, 2004

(54) METHOD OF PERFORMING OPERATING SETTINGS IN HEART RATE MEASUREMENT ARRANGEMENT, AND HEART RATE MEASUREMENT ARRANGEMENT

(75) Inventors: Markku Karjalainen, Kempele (FI); Erkki Loponen, Ruukki (FI)

(73) Assignee: Polar Electro Oy, Kempele (FI)

( * ) Notice: Subject to any disclaimer, the term of this patent is extended or adjusted under 35 U.S.C. 154(b) by 27 days.

(21) Appl. No.: 09/716,630

(22) Filed: Nov. 20, 2000

(30) Foreign Application Priority Data

Nov. 22, 1999 (FI) .............................. 19992484

(51) Int. Cl.⁷ .............................................. A61B 5/024
(52) U.S. Cl. ........................ 600/509; 607/30; 607/32; 600/523
(58) Field of Search .................. 600/300, 509, 600/513, 523; 128/903; 607/30, 32

(56) References Cited

U.S. PATENT DOCUMENTS

| | | | | |
|---|---|---|---|---|
| 4,625,733 A | * | 12/1986 | Saynajakangas | 128/903 |
| 5,189,609 A | * | 2/1993 | Tivig et al. | 600/300 |
| 5,335,664 A | * | 8/1994 | Nagashima | 128/903 |
| 5,365,935 A | * | 11/1994 | Righter et al. | 600/523 |
| 5,400,794 A | * | 3/1995 | Gorman | 128/903 |
| 5,522,396 A | * | 6/1996 | Langer et al. | 128/903 |
| 5,544,661 A | | 8/1996 | Davis et al. | |
| 5,669,392 A | * | 9/1997 | Ljungstrom | 600/300 |
| 5,690,119 A | | 11/1997 | Rytky et al. | |
| 5,701,894 A | * | 12/1997 | Cherry et al. | 128/904 |
| 5,719,825 A | | 2/1998 | Dotter | |
| 5,848,027 A | | 12/1998 | Dotter | |
| 5,957,854 A | * | 9/1999 | Besson et al. | 128/903 |
| 6,259,944 B1 | * | 7/2001 | Margulis et al. | 128/903 |
| 6,282,439 B1 | * | 8/2001 | Ruha | 600/300 |
| 6,315,719 B1 | * | 11/2001 | Rode et al. | 128/903 |
| 6,418,394 B1 | * | 7/2002 | Puolakanaho et al. | 702/139 |

FOREIGN PATENT DOCUMENTS

| | | |
|---|---|---|
| EP | 0809965 | 12/1997 |
| EP | 0842635 | 5/1998 |

* cited by examiner

*Primary Examiner*—Ramesh Krishnamurthy
(74) *Attorney, Agent, or Firm*—Hoffmann & Baron, LLP

(57) ABSTRACT

The invention relates to a method of performing operating settings in a heart rate measurement arrangement, and a heart rate measurement arrangement. Audio frequency information is transmitted to the heart rate measurement arrangement by wireless transmission. The audio frequency information contains setting value information intended to be used in the operation of the heart rate measurement arrangement. In the heart rate measurement arrangement, decoding is performed to decode the received audio frequency information so that the setting value information can be used to control the operation thereof.

25 Claims, 5 Drawing Sheets

METHOD OF PERFORMING OPERATING SETTINGS IN HEART RATE MEASUREMENT ARRANGEMENT, AND HEART RATE MEASUREMENT ARRANGEMENT

BACKGROUND OF THE INVENTION

The invention relates to a method of performing operating settings in a heart rate measurement arrangement.

The invention relates to heart rate monitors. The invention is applied to a personal heart rate measurement device measuring non-invasively, which device is used by sport enthusiasts or athletes, for example. The heart rate measurement equipment may be for instance conventional 2-part equipment comprising a heart rate transmitter comprising the EKG electrodes and being most often of a transmitter-belt type, and a receiver unit in telemetric inductive or optical connection therewith, formed as a wristband, comprising for example a microprocessor, a display and a user interface. Alternatively, it may be heart rate measurement equipment integrated as a wristband, in other words there is hence also a sensor, such as the EKG electrodes or a pressure sensor, in the wristband in addition to other parts. Alternatively, the device parts may be integrated to a belt part measuring the heart rate. The sensor may also be an optical sensor measuring the heart rate, or as mentioned, a pressure pulse sensor, although according to the applicant's notions, these two types of sensors are applicable to measurement from the extremities, such as the wrist or fingers of a hand, and not to measurement from the chest.

In this context, the setting values refer to information concerning the user himself/herself or the exercise that the user intends to perform, or other information fed that is fed to the heart rate measurement arrangement and that the heart rate measurement arrangement uses in its operation. One example of the setting values is the heart rate limits. Heart rate limit alarm is used in heart rate monitors to control the exercise by the sport enthusiast, so that the sport enthusiast receives an alarm if the heart rate in the exercise is or falls below the lower limit or if the heart rate is or rises above the upper limit. In other words, the heart rate must be within a particular range in order for the exercise to be sufficiently efficient but not dangerous.

There are prior art ways to transmit setting value information to the heart rate measurement arrangement. The most conventional way involves feeding through the heart rate monitor's own user interface usually implemented by means of buttons. However, for the most part this way is only appropriate when performed by the user himself/herself and not when performed by a coach, for example. Furthermore, a problem is that feeding has to take place in a state at least nearly immobile in order to avoid feeding errors.

The applicant's own patent publication U.S. Pat. No. 5,690,119 discloses a solution in which setting values are transmitted by means of wireless magnetic inductive connection to the receiver unit of the heart rate monitor by a data transmission device connected to a microcomputer. Thus, however, ordinary use of the heart rate monitor is prevented during the setting transmission, because the reel of the wristband receiver unit in the heart rate monitor cannot at that time receive the signal from the transmitter belt. The receiver unit of the heart rate monitor around the wrist must also be taken close to the data transmission device in order for the data transmission to succeed.

BRIEF DESCRIPTION OF THE INVENTION

It is an object of the invention to provide a novel method and measurement arrangement by means of which the problems and drawbacks of prior art solutions are avoided.

To achieve the above-mentioned object a method according to the invention is characterized by transmitting audio frequency information to the heart rate measurement arrangement by using a terminal connected wirelessly to the heart rate measurement arrangement, which audio frequency information contains setting value information intended to be used in the operation of the heart rate measurement arrangement; and by performing decoding in the heart rate measurement arrangement to decode the received audio frequency information to setting value information controlling the operation of heart rate measurement arrangement.

The heart rate measurement arrangement according to the invention, in turn, is characterized in that the heart rate measurement arrangement comprises an audio frequency receiver for receiving audio frequency information from a terminal that can be wirelessly connected to the heart rate measurement arrangement, which audio frequency information contains setting value information intended to be used in the operation of the heart rate measurement arrangement; and that the heart rate measurement arrangement comprises a decoder in connection with the audio frequency receiver for decoding the received audio frequency information to setting value information controlling the operation of the heart rate measurement arrangement.

The basic idea of the invention is to perform the transmission of the setting value information as audio frequency information. The audio frequency may be the audio frequency of the audibility range or the audio frequency of the ultrasonic range.

An advantage of the method and the arrangement according to the invention is particularly that the device receiving setting information, such as a receiver unit of a wristband in the heart rate monitor, does not have to be taken very near the information-feeding device. Transmission of setting values may take place even if the device that receives the setting values, e.g. the wristband receiver unit of a heart rate monitor, is in motion, so that this will not interfere with the normal activities of the user as much as previously. The preferred embodiments of the invention and other implementation ways described in more detail add to the advantages of the invention.

BRIEF DESCRIPTION OF THE DRAWINGS

The invention is now described in more detail in connection with preferred embodiments, with reference to the attached drawings, of which

DETAILED DESCRIPTION OF THE INVENTION

Figure 1:
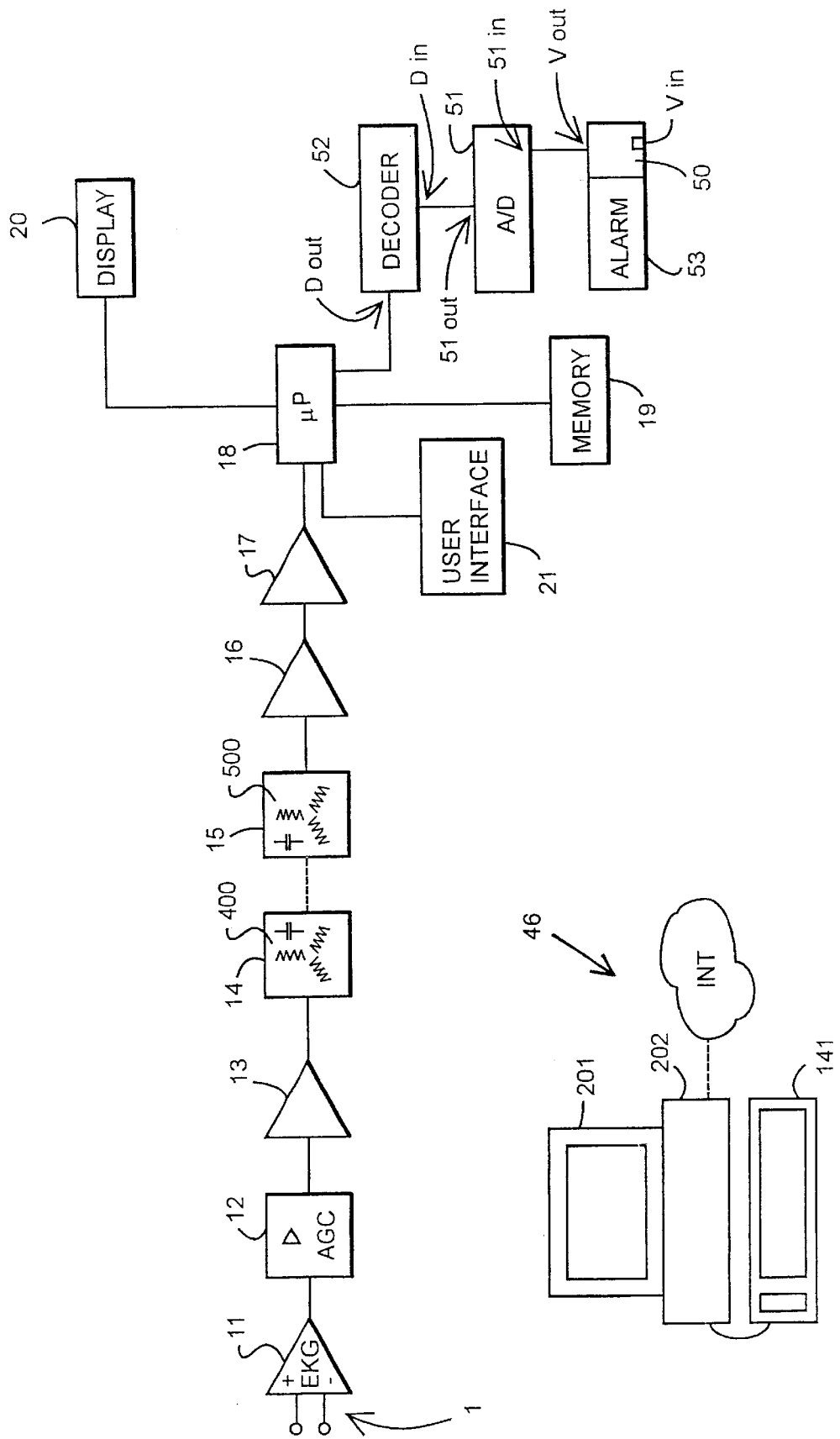
FIG. 1 shows a block diagram of a telemetric heart rate monitor arrangement.
Figure 2:
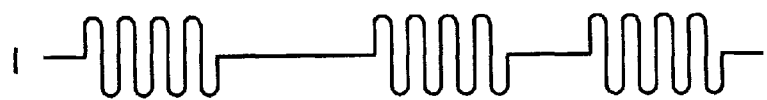
FIG. 2 schematically shows a burst signal to be fed to the magnet coils of a transmitter unit.
Figure 4:
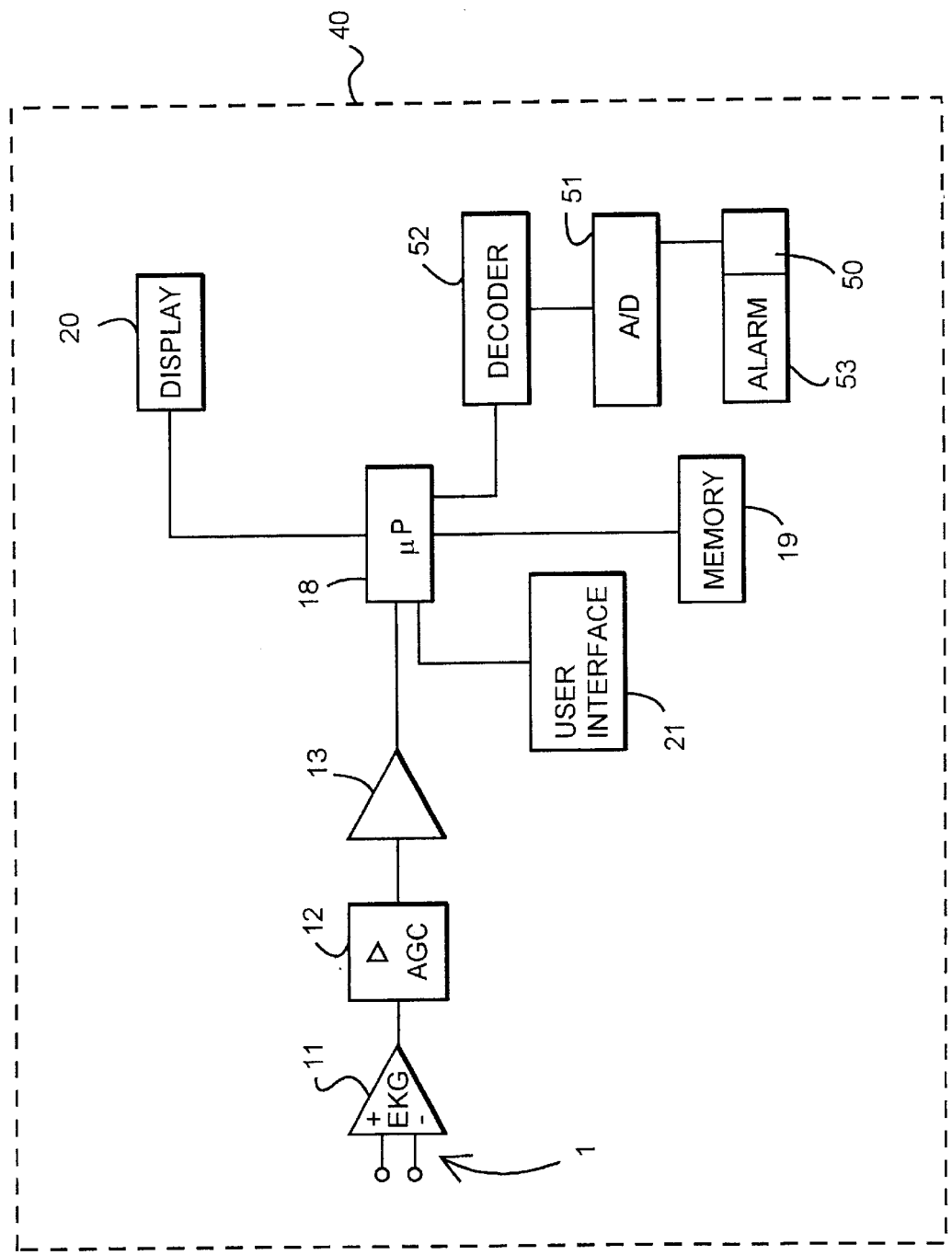
FIG. 4 shows a heart rate monitor arrangement integrated as one unit.

FIG. 1 shows a telemetric heart rate measurement device, i.e. a heart rate monitor arrangement, comprising electrodes 1; an EKG pre-amplifier 11 having differential input poles; an amplifier 12, e.g. an AGC amplifier; a power amplifier 13; a coil structure 14, 15; a pre-amplifier 16; a signal amplifier 17; a data-processing unit 18, e.g. a microcomputer; a memory unit 19; and a display 20, e.g. a liquid crystal display. In FIG. 1, the electrodes 1 of the telemetric heart rate measurement device are connected to the differential input poles of the EKG pre-amplifier. The heart rate signal given by the pre-amplifier 11 is amplified in the amplifier 12, for example in an AGC amplifier, by means of which the power amplifier 13 is controlled, in which power amplifier an alternating current signal, i.e. a burst signal according to FIG. 2 is generated, which controls the coils 14. The magnetic field expressed by the receiver coils 15 is amplified in the pre-amplifier 16, from where the signal is taken to the signal amplifier 17. The output signal of the signal amplifier 17 is processed in the data-processing unit 18, which stores at the measuring stage the heart rate information it has computed in the memory unit 19 and shows them on the display 20. Further, the receiver part may comprise a user interface 21, which can be a button system formed of one or more buttons. The data-processing unit 18 may be for example a microprocessor. In addition, a device B comprises parts 50 to 52, which particularly relate to the implementation of functions according to the invention, in other words they relate to receiving and processing audio frequency information. In FIGS. 1 and 4, the arrangement comprises a sound producer 53, which is preferably a piezoelement.

The device parts 1 to 14 belong to a measuring and transmitter part A. The apparatus parts 15 to 21 and the parts 50 to 52 belong to a receiver part B. Naturally, the transmitter part A and the receiver B may also comprise some other parts in addition to what was mentioned above. The measurement and transmitter part A and the receiver part B together form part of the heart rate monitor arrangement.

Referring to FIGS. 1 to 2, the transmitter A of the heart rate measurement devices sends a burst of 5 kHz, for example, every time it detects an EKG signal. The transmitter circuit of the transmitter unit A is formed of a resonance circuit the activation of which is controlled by the heart rate. In the parallel resonance circuit, capacitance is required in addition to the coil 14. The receiver unit B calculates the heart beat frequency, i.e. on the basis of the time difference of the heart rate signals sent successively, i.e. on the basis of the time difference of the bursts, whereby the information to be sent, i.e. the heart rate, i.e. the heart beat frequency is included in the transmission, being encoded to the time between the burst sets.

Figure 3:
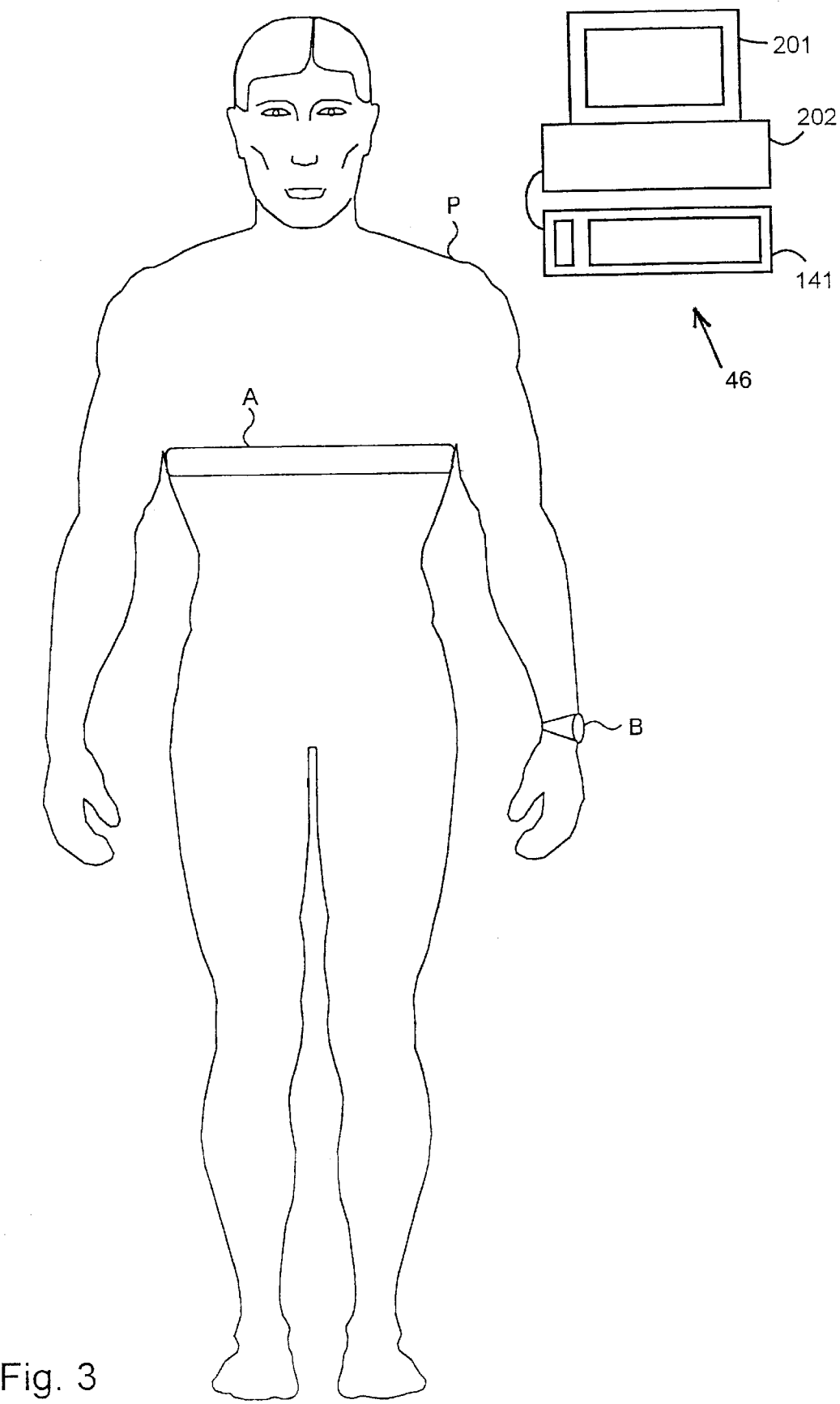
FIG. 3 shows a transmitter unit on a person's chest and a receiver unit around a person's wrist.

Referring to FIG. 3, the devices are most frequently such that the heart rate information measurement and transmitter unit A is around the chest of a person P as a transmitter belt A, from which the measurement information is telemetrically by means of inductive connection 14, 15 of FIG., 1 transmitted wirelessly to the receiver unit B, which is implemented as a receiver wristband around the wrist of person P. In cycling use, the receiver unit B may be attached to the handlebar of a bicycle, for example.

In addition to the one-part device version shown by FIG. 1, the version may be as shown in FIG. 4, this version being partly indicated by broken line 40, which means that the device parts may be integrated to a single housing 40, for example to the electrode belt A or the wristband B. There is no separate transmitter unit or receiver unit in these versions, because the device parts are integrated as one entity, i.e. in practice, the electrodes have been integrated to the same unit as the data-processing unit. Naturally, no coils 14 to 15 and not all amplifiers 16, 17 according to FIG. 1 are required for these version. In FIG. 4, the device comprises structural parts 1 to 13 and 18 to 21, as well as 50 to 52. Transmission is not even necessary if a mere real-time display function is sufficient and no heart rate measurement information needs to be transmitted, i.e. sent, to the microcomputer of the coach, for example. In the following, the invention will be described mainly referring to the more conventional 2-part version according to FIG. 1.

The actual object of the invention relates to a new way of feeding the setting value information to the heart rate measurement arrangement.

FIG. 1 also indicates an external information feeding means, such as a microcomputer 46 or the like terminal 46, and in connection therewith a feeding device 141, such as a button system or other user interface 141, through which setting value information relating to heart rate limits, for example, can be fed to part B of the heart rate monitor arrangement, i.e. to the heart rate receiver unit. In a preferred embodiment, when audio frequency information is sent to the heart rate measurement arrangement, a computer provided with an audio frequency generator 144 is used as the terminal 46. The structure and compatibility of the audio frequency generator 144 and the microcomputer 46, i.e. the terminal 46, are known as such, so that for these aspects reference is made to the literature in the field. In FIGS. 1, 3 and 4 the terminal 46 comprises a display 201, a central unit 202 and a user interface 141.

Figure 6:
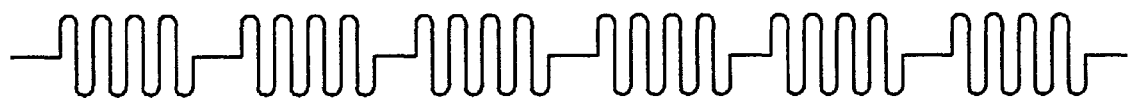
FIG. 6 shows an audio frequency signal in an analogue form.

The heart rate measurement arrangement, most preferably the receiver unit B of the heart rate measurement arrangement, comprises in turn an audio frequency receiver 50 comprising an input V in and an output V out. Further, the arrangement comprises an A/D converter 51, which converts the analogue audio signal into a digital one. The A/D converter 51 comprises an input 51 in and an output 51 out. The output V out of the audio frequency receiver V is connected to the input 51 in of the A/D converter. In addition, the arrangement comprises a decoder 52 comprising an input D in and an output and D out. The output 51 out of the A/D converter is connected to the input D in of the decoder D. The decoder 52 is in connection with the information processor or a similar controlling device part 18, such as a microprocessor, in order for the receipt, conversion, decoding and the like measures to function and so that the received, converted and decoded information can be stored in the memory 19. The decoder finds out the contents of the audio frequency signal, in other words finds out what the audio frequency signal contains. Before decoding, the A/D converter converts each single analogue of the audio frequency signal of FIG. 6 into a bit string of one bit each in such a way that in a preferred embodiment each signal part with a high amplitude is interpreted to have the value binary 1, while the signal parts with low amplitudes are interpreted to have the value binary 0. Signal parts. FIG. 6 shows 6 high signal parts and 6 low signal parts taking turns with the high ones. In other words, above the setting value information is encoded to the amplitude of the audio frequency signal, which is interpreted as value 1 or 0 of the binary string, which string, in turn, is interpreted with the decoder 52. In a second preferred embodiment, the audio frequency information may be encoded to the frequency of the audio frequency signal for example in such a way that the higher frequency is interpreted as binary value 1 and the low frequency is interpreted as binary value 0. The decoder 52 interprets the binary signal. The terminal 46 is provided with an encoder, which operates according to the same rules as the decoder 52 in the heart rate measurement arrangement.

Figure 7:
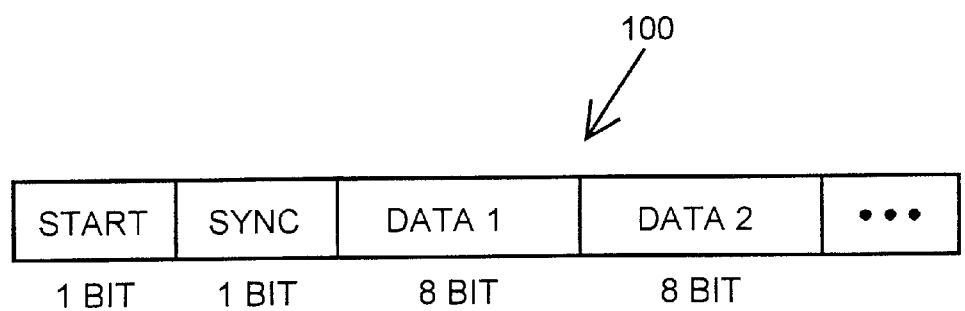
FIG. 7 shows the contents of an audio frequency signal in a digital form.

FIG. 7 shows the contents of a bit stream 100 received from the A/D converter, which bit stream comprises in a preferred embodiment a START pulse, transmission of the audio frequency information of a SYNC pulse and a receiver for synchronization, and in addition, for example two data cycles DATA 1 and DATA 2. The length of the START pulse and the SYNC pulse may be short in both, for example of a length of one bit. The length of the data pulses DATA 1 and DATA 2, which contain setting value information, is longer, for instance 8 bits in both cases.

The analogue signal as A/D converted shown in FIG. 6 is a binary string 101010101010, the first bit of which is the START bit of FIG. 7; the second bit is a SYNC bit; the next eight bits are the setting value information section DATA 1, and the remaining two bits are the first two bits from the second setting value information section DATA 2.

The method is carried out in such a way that by using the terminal 46 in wireless transmission connection to the heart rate measurement arrangement, audio frequency information is transmitted to the heart rate measurement arrangement, which information contains setting value information intended to be used in the operation of the heart rate measurement arrangement. In a preferred embodiment the audio frequency information contains one or more of the following setting value information sections: upper limit of the heart rate alarm, lower limit of the heart rate alarm, sex of the user, age of the user, weight of the user, duration of the exercise interval, number of the exercise intervals to be repeated, height of the user, time, date, wake-up setting. Some other setting value information section may also be used, but according to the applicant's notions, the above setting value information sections are the most necessary in the control of the heart rate measurement arrangement operation.

After the heart rate measurement arrangement has received the audio frequency information containing one or more of the above setting value information sections, decoding is performed in the heart rate measurement arrangement by means of the decoder 52 to decode the received audio frequency information to setting value information controlling the operation of the heart rate measurement arrangement. The setting value information is stored in the memory 19, from which the microprocessor 18 or a similar controlling device part utilizes it in the operation of the heart rate measurement arrangement. The memory 19 may also be a memory other than said memory 19, which is in the example of the figures also a memory for the heart rate information that has been measured.

The terminal 46 may in a preferred embodiment be an application program, by means of which the coach, for example, feeds setting values with the button system 46. The application program can for example ask the age and sex of the user and desired heart rate limits to be set for the user. This information is fed to the terminal by means of the user interface 46, and finally, a transmission command is given, whereby the terminal commands an audio card 146 or similar device part to perform audio frequency transmission.

In a preferred embodiment, the entity of two or more setting value information sections, such as the lower limit of the heart rate and the upper limit of the heart rate, is made ready, and only after that the audio frequency transmission, i.e. sending is performed. Said embodiment is quicker and simpler than the transmission of a single setting value information immediately after the feeding.

Audio range refers in this application to frequencies between 100 Hz to 50 kHz in the frequency range. In other words, this refers to the audio frequency of 100 Hz to 20 kHz in the audibility range or to the audio frequency of 20 kHz to 50 kHz in the ultra sonic range.

Figure 5:
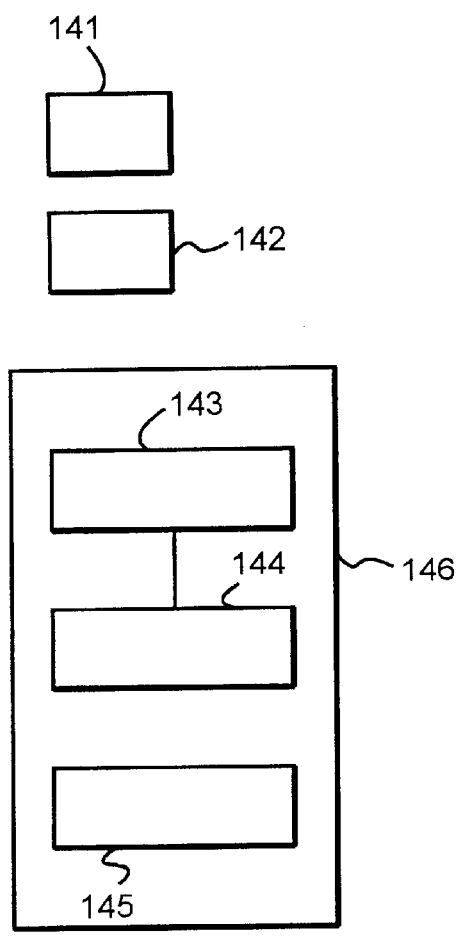
FIG. 5 shows a simplified block diagram of a terminal.

FIG. 5 illustrates essential parts of the terminal 46. The terminal 46 may be implemented for example by means of a conventional PC. The terminal 46 comprises the user interface 141 intended for the feed of setting value information, and a processor 142 controlling the operation of the terminal. In addition, the terminal 46 comprises a sound processor 143, i.e. what is called a sound CPU 143, and an audio frequency generator 144, the sound processor being connected to control the audio frequency generator. In addition, the terminal 46 comprises a sound processor 145, which is for example a loudspeaker, connected to an audio frequency generator 144. The structural part 143 to 145, i.e. the sound processor 143, the audio frequency generator 144 and the sound source 145, is in a preferred embodiment components on the sound card 146. The terminal functions in such a way that setting value information is given by means of the user interface, such as the button system 141, for example such a setting value information section that the heart rate lower limit is 120 heart beats per minute. The terminal processor 142 controls the sound processor 143 by telling the sound processor 143 at which point of time and at which frequency sound should be transmitted. The sound processor interprets the message and converts the instruction into a form that is understood by the audio frequency generator 144. The audio frequency generator converts the digital control received from the sound processor into an analogue signal, which is converted into an audio frequency signal by the sound producer 145, such as a loudspeaker, the audio frequency signal being received by the sound receiver in the heart rate measurement arrangement.

Going back to the device description of the heart rate measurement arrangement it is noted that the heart rate measurement arrangement comprises a sensor structure 1, such as an electrode structure, for measuring the heart rate signal from the body of a person. If it were a question of measurement of a pressure pulse due to heartbeat and detected in an artery, a pressure pulse sensor would be used instead of electrodes.

In addition, the arrangement comprises the signal-processing means 11 to 13 and 16 to 17 connected to a sensor structure 1, and calculation means 18, such as a microprocessor 18, connected to the signal-processing means, and a display 20 connected to the calculation means 18 and/or a memory 19 for showing and/or storing the heart rate information. According to the invention, the heart rate measurement arrangement comprises an audio frequency receiver for receiving audio frequency information from a terminal wirelessly connectable to the heart rate measurement arrangement, which audio frequency information contains setting value information that is intended to be used in the operation of the heart rate measurement arrangement. The heart rate measurement arrangement comprises a decoder 52 connected to the audio frequency receiver for decoding audio frequency information to setting value information controlling the operation of the heart rate measurement arrangement.

In the preferred embodiment shown in FIG. 1, the heart rate measurement arrangement comprises two separate structural units A and B connected wirelessly to each other in such a way that the first structural unit A comprises a sensor structure 1, a part of the signal-processing means, i.e. the signal-processing means 11 to 13, and a transmitter structure 14 connected to the signal-processing means, which performs wireless data transmission. In this-preferred embodiment the arrangement is such that the second structural part B comprises a receiver structure 15, which uses wireless data transmission, for receiving heart rate measurement information from the receiver structure 14, and in addition, the second structural unit B comprises the second part of the signal-processing means, i.e. means 16 to 17, connected to the receiver structure 15, and in addition, this second structural part comprises a calculating unit, a display 20 and/or a memory 19, and an audio frequency receiver 50 and a decoder 52, as well as an A/D converter. Preferably, said second structural unit is a wristband unit B in FIG. 3. In the preferred embodiment the arrangement is such that the transmitter structure in the first structural unit A comprises a resonance circuit 400 for inductive transmission. Correspondingly, in the preferred embodiment the receiver structure 15 in the second structural unit B comprises a resonance circuit 500 for inductive receipt. The resonance circuit 400, correspondingly 500 is preferably a parallel resonance circuit to the coil and the capacitor.

An embodiment alternative to the 2-part heart rate measurement arrangement according to FIG. 1 is shown in FIG. 4, in which the heart rate measurement arrangement has at least principally one part in such a way that the sensor structure 1 is in the same structural unit as the signal-processing means 11 to 13, the heart rate information calculation means 18 and the display 20 intended for showing and/or storing heart rate information, and/or the memory 19, and the audio frequency receiver 50 and the decoder 52, and the A/D converter 51. Preferably, said same structural unit is a wristband unit, as in FIG. 3, but comprising among other things a sensor structure 1, as noted, which are in FIG. 1 in a chest electrode belt. In this embodiment, the sensor structure 1 may be a sensor measuring the pressure pulse of an artery instead of a two-electrode electrode structure measuring an electric potential difference. However, measurement of the potential difference implemented by means of electrodes is also possible.

If the user does not separately feed setting value information, in one preferred embodiment the selection of setting value information is performed from a memory, which is connected to the terminal or at least temporarily connectable thereto, in other words the user of the terminal, such as a coach, selects a desired value from a set of suitable values. In another preferred embodiment, selection of setting value information is performed by charging the setting value information with the terminal 46 from the Internet information network, INT, or from another information network INT, such as the Extranet or Internet information network. A suitable data transmission member may be used for charging, for example a network information card or modem. These embodiments facilitate the use of the arrangement and enable easy formation of even complex combinations of setting value information.

The invention may also be applied to measurement of another biosignal.

Transmission of audio frequency information may also in a preferred embodiment of the invention be bidirectional, which allows utilization of the unidirectional solution known from publications U.S. Pat No. 5,719,825 and 5,848,027 for transmitting a biosignal measured from the body, such as heart rate information, from the monitor to the terminal. As for detailed implementation, reference is made to said publications, the contents of which is incorporated by reference herein. As noted, in said preferred embodiment the heart rate measurement arrangement comprises means for encoding and transmitting heart rate information to the terminal as audio frequency information. Said means may comprise an encoder, a D/A converter and a sound source 53, for example. The terminal 46, in turn, comprises an audio frequency receiver and a decoder. The operation would be in a way directed to the opposite direction compared with what was presented concerning setting value information.

It is obvious to a person skilled in the art that when the technology develops further, the basic idea of the invention can be implemented in many different ways. The invention and embodiments thereof are thus not limited to the above-described examples but may vary within the scope of the claims.

What is claimed is:

1. A method of providing operational settings to a heart rate measurement arrangement, said heart rate measurement arrangement including a receiver element comprising a piezo element capable of receiving or generating an audible sound signal, comprising:

wirelessly transmitting an audible sound signal including audio frequency information containing setting value information from a terminal to said receiver element, said setting value information being usable in the operation of said heart rate measurement arrangement;

decoding said audio frequency information in said heart rate measurement arrangement; and storing said setting value information for use during operation of said heart rate measurement arrangement.

2. A method according to claim 1, wherein the audio frequency information contains one or more of the following setting value information sections: upper limit of the heart rate alarm, lower limit of the heart rate alarm, sex of the user, age of the user, weight of the user, duration of the exercise interval, number of exercise intervals to be repeated, height of the user, time, date, wake-up setting.

3. A method according to claim 1, wherein the heart rate measurement arrangement receives the audio frequency information by means of an element also used for giving a sound signal in the heart rate measurement arrangement as soon as the heart rate limit is achieved during the exercise.

4. A method according to claim 1, wherein a computer provided with an audio frequency generator is used as the terminal in transmitting the audio frequency information to the heart rate measurement arrangement.

5. A method according to claim 1, wherein desired setting information is selected using the terminal, and the terminal encodes the selected setting information to transmit it as audio frequency information to the heart rate measurement arrangement.

6. A method according to claim 1, including selecting setting value information from a memory which is connected to the terminal or at least temporarily connectable thereto.

7. A method according to claim 1, including selecting setting value information by charging the setting value information by means of the terminal from the Internet information network.

8. A method according to claim 1, wherein before the terminal transmits audio frequency information containing setting value information to the heart rate measurement arrangement, the terminal gives an audio frequency signal to inform the user.

9. A method according to claim 1, wherein when the setting value information has been transmitted to the heart rate measurement arrangement, checking of the transmitted setting value information is performed automatically or beginning with a command by the user, in which checking a display of the heart rate measurement arrangement shows the transmitted setting value information to the user.

10. A heart rate measurement arrangement comprising:
- a sensor structure for measuring a heart rate signal from the body of a person;
- a signal-processing means for processing a signal received from the sensor structure;
- a calculation unit connected to the signal-processing means;
- means connected to the calculation unit for showing and/or storing heart rate information;
- an audio frequency receiver comprising a piezo element for generating an audible sound signal and for wirelessly receiving an audible sound signal including audio frequency information containing setting value information from a terminal; and
- a decoder in connection with the audio frequency receiver for decoding the received audio frequency information containing said setting value information.

11. A heart rate measurement arrangement according to claim 10, wherein the audio frequency information to be received to the heart rate measurement arrangement contains one or more of the following setting value information sections: upper limit of the heart rate alarm, lower limit of the heart rate alarm, sex of the user, age of the user, weight of the user, duration of the exercise interval, number of the exercise intervals to be repeated, height of the user, time, date, wake-up setting.

12. A heart rate measurement arrangement according to claim 10, wherein the audio frequency receiver comprises an element also used for giving a sound signal as soon as the heart rate limit is achieved during the exercise.

13. A heart rate measurement arrangement according to claim 10, wherein said audio frequency receiver is incorporated as part of a wristband adapted to be worn by a user, against his/her body.

14. A heart rate measurement arrangement according to claim 10, further comprising a wristband part which comprises at least a part of the signal-processing means, calculation means, a display and/or a memory, an audio frequency receiver and a decoder.

15. A heart rate measurement arrangement according to claim 10, wherein the heart rate measurement arrangement has at least principally one part in such a way that the sensor structure is in the same structural unit as the signal-processing means, the heart rate calculation means and the display intended for showing and/or storing heart rate information and/or the memory, and the audio frequency receiver and the decoder.

16. A heart rate measurement arrangement according to claim 15, wherein said same structural unit is a wristband unit.

17. A heart rate measurement arrangement according to claims 10, wherein the heart rate measurement arrangement comprises two separate structural units connected wirelessly to each other in such a way that the first structural unit is provided with said sensor structure, a part of the signal-processing means and a transmitter structure in connection therewith for performing wireless data transmission; and the second structural part is provided with a receiver structure using wireless data transmission for receiving heart rate measurement information from the receiver structure, a second part of the signal-processing means connected to the receiver structure, said calculation unit, a display and/or a memory, and said audio frequency receiver and said decoder.

18. A heart rate measurement arrangement according to claim 17, wherein said second structural unit is a wristband unit.

19. A heart rate measurement arrangement according to claim 17, wherein the transmitter structure in the first structural unit comprises a resonance circuit for inductive transmission.

20. A heart rate measurement arrangement according to claim 17, wherein the receiver structure in the second structural unit comprises a resonance circuit for inductive receipt.

21. A heart rate measurement arrangement according to claim 10, wherein the heart rate measurement arrangement comprise a memory for storing the decoded setting value information in the heart rate measurement arrangement.

22. A heart rate measurement arrangement according to claim 10, wherein in the audio frequency signal to be received to the heart rate measurement arrangement, the setting value information is encoded to the amplitude of the audio frequency signal.

23. A heart rate measurement arrangement according to claim 10, wherein in the audio frequency signal to be received to the heart rate measurement arrangement, the setting value information is encoded to the frequency of the audio frequency signal.

24. A method of providing operational settings to a heart rate measurement arrangement, said heart rate measurement arrangement including a receiver element comprising a piezo element capable of receiving or generating an audible sound signal, comprising:
- wirelessly transmitting an audible sound signal including audio frequency information containing setting value information from a terminal to said receiver element, wherein said receiver element is a piezo element, said setting value information being usable in the operation of said heart rate measurement arrangement such that said piezo element produces an audible sound signal as soon as a heart rate limit is achieved during exercise;
- decoding said audio frequency information in said heart rate measurement arrangement; and
- storing said setting value information for use during operation of said heart rate measurement arrangement.

25. A heart rate measurement arrangement comprising:
- a sensor structure for measuring a heart rate signal from the body of a person;
- a signal processor for processing a signal received from the sensor structure;
- a calculation unit connected to the signal processor;
- means connected to the calculation unit for showing and/or storing heart rate information;
- an audio frequency receiver comprising a piezo element for generating an audible sound signal and for wirelessly receiving an audible sound signal containing audio frequency information containing setting value information from a terminal;
- a decoder in connection with the audio frequency receiver for decoding the received audio frequency information containing said setting value information; and
- an element for producing an audible sound signal as soon as a heart rate limit is achieved during exercise.

* * * * *